(12) United States Patent
Hayes

(10) Patent No.: US 10,010,405 B2
(45) Date of Patent: Jul. 3, 2018

(54) HAPTIC DEVICES FOR INTRAOCULAR LENS

(71) Applicant: Anew IOL Technologies, Inc., Bristo, TN (US)

(72) Inventor: Anna S. Hayes, Newton Centre, MA (US)

(73) Assignee: Anew AOL Technologies, Inc., Bristol, TN (US)

(*) Notice: Subject to any disclaimer, the term of this patent is extended or adjusted under 35 U.S.C. 154(b) by 0 days.

(21) Appl. No.: 14/808,412

(22) Filed: Jul. 24, 2015

(65) Prior Publication Data
US 2015/0327991 A1 Nov. 19, 2015

Related U.S. Application Data

(63) Continuation-in-part of application No. 12/626,473, filed on Nov. 25, 2009, now Pat. No. 9,439,755.

(60) Provisional application No. 62/028,375, filed on Jul. 24, 2014, provisional application No. 61/184,655, filed on Jun. 5, 2009, provisional application No. 61/157,781, filed on Mar. 5, 2009, provisional application No. 61/118,085, filed on Nov. 26, 2008.

(51) Int. Cl.
*A61F 2/16* (2006.01)

(52) U.S. Cl.
CPC ...... *A61F 2/1613* (2013.01); *A61F 2002/169* (2015.04)

(58) Field of Classification Search
CPC ................................................ A61F 2002/169
See application file for complete search history.

(56) References Cited

U.S. PATENT DOCUMENTS

| | | | |
|---|---|---|---|
| 3,673,616 A | 7/1972 | Fedorov et al. |
| 3,866,249 A | 2/1975 | Flom |
| 3,906,551 A | 9/1975 | Otter |
| 3,913,148 A | 10/1975 | Potthast |
| 3,975,779 A | 8/1976 | Richards et al. |
| 4,014,049 A | 3/1977 | Richards et al. |
| 4,053,953 A | 10/1977 | Flom et al. |
| 4,073,014 A | 2/1978 | Poler |

(Continued)

FOREIGN PATENT DOCUMENTS

| | | |
|---|---|---|
| EP | 1961399 | 8/2008 |
| EP | 2111822 | 9/2014 |

(Continued)

OTHER PUBLICATIONS

Zaldivar et al.; "The Current Status of Phakic Intraocular Lenses;" International Opthamology Clinics; vol. 36, No. 4; 1996; pp. 107-111.

(Continued)

*Primary Examiner* — Leslie Lopez
(74) *Attorney, Agent, or Firm* — Remenick PLLC

(57) ABSTRACT

A haptic for fixation to, and manufacture in conjunction with, an intraocular lens to be implanted in the natural lens capsule of the human eye is disclosed. The haptic secures the lens in an appropriate position within the natural capsule so as to provide optimal visual acuity through the aphakic lens. The haptic is designed to position the lens neutrally, anteriorly or posteriorly within the lens envelope. The haptic has an anterior retention ring and a posterior retention ring.

18 Claims, 9 Drawing Sheets

(56) References Cited

U.S. PATENT DOCUMENTS

| | | |
|---|---|---|
| 4,087,866 A | 5/1978 | Choyce et al. |
| 4,092,743 A | 6/1978 | Kelman |
| 4,102,567 A | 7/1978 | Cuffe et al. |
| 4,136,406 A | 1/1979 | Norris |
| 4,141,973 A | 2/1979 | Balazs |
| 4,159,546 A | 7/1979 | Shearing |
| 4,173,281 A | 11/1979 | Trought |
| 4,174,543 A | 11/1979 | Kelman |
| 4,190,049 A | 2/1980 | Hager et al. |
| 4,198,980 A | 4/1980 | Clark |
| 4,215,440 A | 8/1980 | Worst |
| 4,240,163 A | 12/1980 | Galin |
| 4,242,760 A | 1/1981 | Rainin |
| 4,244,060 A | 1/1981 | Hoffer |
| 4,249,271 A | 2/1981 | Poler |
| 4,251,887 A | 2/1981 | Anis |
| 4,254,509 A | 3/1981 | Tennant |
| 4,254,510 A | 3/1981 | Tennant |
| 4,269,307 A | 5/1981 | LaHaye |
| 4,270,230 A | 6/1981 | Poler |
| 4,280,232 A | 7/1981 | Hummel |
| 4,285,072 A | 8/1981 | Morcher et al. |
| 4,325,375 A | 4/1982 | Nevyas |
| 4,326,306 A | 4/1982 | Poler |
| 4,349,027 A | 9/1982 | DiFrancesco |
| 4,363,142 A | 12/1982 | Meyer |
| 4,363,143 A | 12/1982 | Callahan |
| 4,366,582 A | 1/1983 | Faulkner |
| 4,370,760 A | 2/1983 | Kelman |
| 4,409,691 A | 10/1983 | Levy |
| 4,423,809 A | 1/1984 | Mazzocco |
| 4,435,855 A | 3/1984 | Pannu |
| 4,441,217 A | 4/1984 | Cozean, Jr. |
| 4,446,581 A | 5/1984 | Blake |
| 4,451,938 A | 6/1984 | Kelman |
| 4,463,458 A | 8/1984 | Seidner |
| 4,468,820 A | 9/1984 | Uhler et al. |
| 4,480,340 A | 11/1984 | Shepard |
| 4,494,254 A | 1/1985 | Lopez |
| 4,504,981 A | 3/1985 | Walman |
| 4,508,216 A | 4/1985 | Kelman |
| 4,517,295 A | 5/1985 | Bracke et al. |
| 4,527,294 A | 7/1985 | Heslin |
| 4,530,117 A | 7/1985 | Kelman |
| 4,534,069 A | 8/1985 | Kelman |
| 4,536,895 A | 8/1985 | Bittner |
| 4,573,998 A | 3/1986 | Mazzocco |
| 4,575,374 A | 3/1986 | Anis |
| 4,576,607 A | 3/1986 | Kelman |
| 4,581,033 A | 4/1986 | Callahan |
| 4,585,456 A | 4/1986 | Blackmore |
| 4,591,358 A | 5/1986 | Kelman |
| 4,608,049 A | 8/1986 | Kelman |
| 4,615,703 A | 10/1986 | Callahan et al. |
| 4,619,256 A | 10/1986 | Horn |
| 4,624,669 A | 11/1986 | Grendahl |
| 4,629,460 A | 12/1986 | Dyer |
| 4,634,423 A | 1/1987 | Bailey, Jr. |
| 4,638,056 A | 1/1987 | Callahan et al. |
| 4,655,775 A | 4/1987 | Clasby, III |
| 4,676,792 A | 6/1987 | Praeger |
| 4,676,794 A | 6/1987 | Kelman |
| 4,684,014 A | 8/1987 | Davenport |
| 4,687,484 A | 8/1987 | Kaplan |
| 4,700,638 A | 10/1987 | Przewalski |
| 4,701,181 A | 10/1987 | Arnott |
| 4,704,123 A | 11/1987 | Smith |
| 4,710,195 A | 12/1987 | Giovinazzo |
| 4,710,795 A | 12/1987 | Nippert et al. |
| 4,711,638 A | 12/1987 | Lindstrom |
| 4,718,906 A | 1/1988 | Mackool |
| 4,736,836 A | 4/1988 | Alongi et al. |
| 4,764,169 A | 8/1988 | Grendahl |
| 4,769,035 A | 9/1988 | Kelman |
| 4,778,464 A | 10/1988 | Sergienko et al. |
| 4,781,719 A | 11/1988 | Kelman |
| 4,787,902 A | 11/1988 | Sheets et al. |
| 4,795,460 A | 1/1989 | Anis |
| 4,795,462 A | 1/1989 | Grendahl |
| 4,804,361 A | 2/1989 | Anis |
| 4,816,032 A | 3/1989 | Hetland |
| 4,828,558 A | 5/1989 | Kelman |
| 4,834,750 A | 5/1989 | Gupta |
| 4,842,600 A | 6/1989 | Feaster |
| 4,852,566 A | 8/1989 | Callahan et al. |
| 4,863,462 A | 9/1989 | Fedorov et al. |
| 4,863,463 A | 9/1989 | Tjan |
| 4,863,465 A | 9/1989 | Kelman |
| 4,871,363 A | 10/1989 | Kelman |
| 4,872,876 A | 10/1989 | Smith |
| 4,878,911 A | 11/1989 | Anis |
| 4,888,012 A | 12/1989 | Horn et al. |
| 4,919,130 A | 4/1990 | Stoy et al. |
| 4,923,296 A | 5/1990 | Erickson |
| 4,932,970 A | 6/1990 | Portney |
| 4,950,290 A | 8/1990 | Kamerling |
| 4,994,080 A | 2/1991 | Shepard |
| 4,995,714 A | 2/1991 | Cohen |
| 5,002,568 A | 3/1991 | Katzen |
| 5,019,098 A | 5/1991 | Mercier |
| 5,047,052 A | 9/1991 | Dubroff |
| 5,076,684 A | 12/1991 | Simpson et al. |
| 5,098,444 A | 3/1992 | Feaster |
| 5,100,226 A | 3/1992 | Freeman |
| 5,108,429 A | 4/1992 | Wiley |
| 5,118,452 A | 6/1992 | Lindsey et al. |
| 5,123,905 A | 6/1992 | Kelman |
| 5,133,747 A | 7/1992 | Feaster |
| 5,133,749 A | 7/1992 | Nordan |
| 5,152,789 A | 10/1992 | Willis |
| 5,166,711 A | 11/1992 | Portney |
| 5,171,320 A | 12/1992 | Nishi |
| 5,176,686 A | 1/1993 | Poley |
| 5,178,636 A | 1/1993 | Silberman |
| 5,192,319 A | 3/1993 | Worst |
| 5,197,981 A | 3/1993 | Southard |
| 5,199,559 A | 4/1993 | Dark |
| 5,229,797 A | 7/1993 | Futhey et al. |
| 5,236,452 A | 8/1993 | Nordan |
| 5,258,025 A | 11/1993 | Fedorov et al. |
| 5,266,074 A | 11/1993 | Nishi et al. |
| 5,281,227 A | 1/1994 | Sussman |
| 5,361,780 A | 11/1994 | Kellan |
| 5,366,501 A | 11/1994 | Langerman |
| 5,370,652 A | 12/1994 | Kellan |
| 5,405,386 A | 4/1995 | Rheinish et al. |
| 5,425,734 A | 6/1995 | Blake |
| D360,068 S | 7/1995 | Hambleton et al. |
| 5,443,506 A | 8/1995 | Garabet |
| 5,468,246 A | 11/1995 | Blake |
| 5,476,512 A | 12/1995 | Sarfarazi |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,507,806 A | 4/1996 | Blake |
| 5,522,890 A | 6/1996 | Nakajima et al. |
| 5,549,670 A | 8/1996 | Young et al. |
| 5,593,436 A | 1/1997 | Langerman |
| 5,628,794 A | 5/1997 | Lindstrom |
| 5,643,275 A | 7/1997 | Blake |
| D382,399 S | 8/1997 | Hambleton et al. |
| 5,674,282 A | 10/1997 | Cumming |
| 5,682,223 A | 10/1997 | Menezes et al. |
| 5,697,973 A | 12/1997 | Peyman et al. |
| 5,709,220 A | 1/1998 | Kellan |
| 5,713,958 A | 2/1998 | Weiser |
| 5,772,667 A | 6/1998 | Blake |
| 5,782,911 A | 7/1998 | Herrick |
| 5,800,532 A | 9/1998 | Lieberman |
| 5,847,802 A | 12/1998 | Menezes et al. |
| 5,855,605 A | 1/1999 | Herrick |
| 5,919,229 A | 7/1999 | Portney |
| 5,928,282 A | 7/1999 | Nigam |

(56) References Cited

U.S. PATENT DOCUMENTS

| | | |
|---|---|---|
| 5,947,976 A | 9/1999 | Van Noy et al. |
| 5,976,150 A | 11/1999 | Copeland |
| 6,010,510 A | 1/2000 | Brown et al. |
| 6,013,101 A | 1/2000 | Israel |
| 6,015,435 A | 1/2000 | Valunin et al. |
| 6,051,024 A | 4/2000 | Cumming |
| 6,083,261 A | 7/2000 | Callahan et al. |
| 6,090,141 A | 7/2000 | Lindstrom |
| 6,096,077 A | 8/2000 | Callahan et al. |
| 6,110,202 A | 8/2000 | Barraquer et al. |
| 6,120,148 A | 9/2000 | Fiala et al. |
| 6,129,723 A | 10/2000 | Anderson et al. |
| 6,142,999 A | 11/2000 | Brady et al. |
| 6,152,958 A | 11/2000 | Nordan |
| 6,197,059 B1 | 3/2001 | Cumming |
| 6,203,549 B1 | 3/2001 | Waldock |
| 6,224,628 B1 | 5/2001 | Callahan et al. |
| 6,241,777 B1 | 6/2001 | Kellan |
| 6,261,321 B1 | 7/2001 | Kellan |
| 6,277,146 B1 | 8/2001 | Peyman et al. |
| 6,299,641 B1 | 10/2001 | Woods |
| 6,398,786 B1 | 6/2002 | Sesic |
| 6,443,985 B1 | 9/2002 | Woods |
| 6,447,519 B1 | 9/2002 | Brady et al. |
| 6,461,384 B1 | 10/2002 | Hoffmann et al. |
| 6,488,707 B1 | 12/2002 | Callahan et al. |
| 6,488,709 B1 | 12/2002 | Barrett |
| 6,494,911 B2 | 12/2002 | Cumming |
| 6,517,577 B1 | 2/2003 | Callahan et al. |
| 6,533,813 B1 | 3/2003 | Lin et al. |
| 6,537,283 B2 | 3/2003 | Van Noy |
| 6,605,093 B1 | 8/2003 | Blake |
| 6,622,855 B1 | 9/2003 | Callahan et al. |
| 6,623,522 B2 | 9/2003 | Nigam |
| 6,645,246 B1 | 11/2003 | Weinschenk, III et al. |
| 6,666,887 B1 | 12/2003 | Callahan et al. |
| 6,749,633 B1 | 6/2004 | Lorenzo et al. |
| 6,786,928 B2 | 9/2004 | Callahan et al. |
| 6,797,004 B1 | 9/2004 | Brady et al. |
| 6,800,091 B2 | 10/2004 | Callahan et al. |
| 6,921,415 B2 | 7/2005 | Callahan et al. |
| 6,976,989 B1 | 12/2005 | Vincent |
| 7,037,328 B2 | 5/2006 | Vincent |
| 7,037,338 B2 | 5/2006 | Nagamoto |
| 7,063,723 B2 | 6/2006 | Ran |
| 7,125,422 B2 | 10/2006 | Woods et al. |
| 7,179,292 B2 | 2/2007 | Worst et al. |
| 7,198,640 B2 | 4/2007 | Nguyen |
| 7,220,279 B2 | 5/2007 | Nun |
| 7,223,288 B2 | 5/2007 | Zhang et al. |
| 7,279,006 B2 | 10/2007 | Vincent |
| 7,354,451 B2 | 4/2008 | Koch |
| 7,503,938 B2 | 3/2009 | Phillips |
| 7,713,299 B2 | 5/2010 | Brady et al. |
| 8,043,372 B2 | 10/2011 | Bumbalough |
| 2001/0001836 A1 | 5/2001 | Cumming |
| 2001/0044657 A1 | 11/2001 | Kellan |
| 2001/0044857 A1 | 11/2001 | Pham et al. |
| 2002/0055777 A1 | 5/2002 | Cumming et al. |
| 2002/0072673 A1 | 6/2002 | Yamamoto et al. |
| 2002/0072795 A1 | 6/2002 | Green |
| 2002/0095212 A1 | 7/2002 | Boehm |
| 2002/0103536 A1 | 8/2002 | Landreville et al. |
| 2002/0116059 A1 | 8/2002 | Zadno-Azizi et al. |
| 2002/0120331 A1 | 8/2002 | Galin et al. |
| 2002/0161437 A1 | 10/2002 | Zhou et al. |
| 2002/0193877 A1 | 12/2002 | Hoffmann et al. |
| 2003/0033013 A1 | 2/2003 | Callahan et al. |
| 2003/0050695 A1 | 3/2003 | Lin et al. |
| 2003/0065387 A1 | 4/2003 | Callahan et al. |
| 2003/0078655 A1 | 4/2003 | Callahan et al. |
| 2003/0114927 A1 | 6/2003 | Nagamoto |
| 2003/0130732 A1 | 7/2003 | Sarfarazi |
| 2003/0135272 A1* | 7/2003 | Brady ............... A61F 2/16 623/6.37 |
| 2003/0135273 A1 | 7/2003 | Callahan et al. |
| 2003/0149479 A1 | 8/2003 | Snyder et al. |
| 2003/0149480 A1 | 8/2003 | Shadduck |
| 2004/0082994 A1 | 4/2004 | Woods et al. |
| 2004/0215340 A1 | 10/2004 | Messner et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0033308 A1 | 2/2005 | Callahan et al. |
| 2005/0107875 A1 | 5/2005 | Cumming |
| 2005/0251253 A1 | 11/2005 | Gross |
| 2006/0047339 A1 | 3/2006 | Brown |
| 2006/0100704 A1 | 5/2006 | Blake et al. |
| 2006/0142781 A1 | 6/2006 | Pynson et al. |
| 2006/0235515 A1 | 10/2006 | Chassain |
| 2006/0247767 A1 | 11/2006 | Koch |
| 2006/0293694 A1 | 12/2006 | Futamura |
| 2007/0093892 A1 | 4/2007 | Mackool |
| 2007/0213817 A1 | 9/2007 | Esch et al. |
| 2007/0239274 A1 | 10/2007 | Kellan |
| 2008/0161913 A1 | 7/2008 | Brady et al. |
| 2008/0281417 A1 | 11/2008 | Nagamoto |
| 2009/0171458 A1 | 7/2009 | Kellan et al. |
| 2009/0248031 A1 | 10/2009 | Ichinohe et al. |
| 2010/0131059 A1 | 5/2010 | Callahan et al. |
| 2010/0131061 A1 | 5/2010 | Callahan et al. |
| 2010/0152846 A1 | 6/2010 | Vaillant et al. |
| 2010/0179652 A1 | 7/2010 | Yamamoto et al. |
| 2010/0204787 A1 | 8/2010 | Noy |
| 2010/0204788 A1 | 8/2010 | Van Noy |
| 2010/0228260 A1 | 9/2010 | Callahan et al. |
| 2011/0054600 A1 | 3/2011 | Bumbalough |
| 2011/0191086 A1 | 8/2011 | Callahan et al. |
| 2011/0257742 A1 | 10/2011 | Bumbalough et al. |
| 2011/0313522 A1 | 12/2011 | Hayes |
| 2011/0313523 A1 | 12/2011 | Hayes |
| 2012/0010704 A1 | 1/2012 | Bumbalough |
| 2012/0078363 A1 | 3/2012 | Lu |
| 2012/0330415 A1 | 12/2012 | Callahan et al. |

FOREIGN PATENT DOCUMENTS

| | | | |
|---|---|---|---|
| FR | 2997624 | 10/2009 | |
| GB | 2029235 | 3/1980 | |
| GB | 2124500 | 2/1984 | |
| GB | 2165456 | 4/1986 | |
| JP | 61502661 | 11/1985 | |
| JP | 6055131 | 12/1985 | |
| WO | WO9817205 | 4/1998 | |
| WO | WO9929266 | 6/1999 | |
| WO | WO 0078251 A1 * | 12/2000 | ........... A61F 2/1616 |
| WO | WO0078252 | 12/2000 | |
| WO | WO2003017867 | 3/2003 | |
| WO | WO2004082535 | 9/2004 | |
| WO | WO2007117476 | 10/2007 | |
| WO | WO2007134019 | 11/2007 | |
| WO | WO2008108523 | 9/2008 | |
| WO | WO2008108524 | 9/2008 | |
| WO | WO 2009 013421 * | 1/2009 | ............... A61F 2/16 |

OTHER PUBLICATIONS

Neuhann; "Corneal or Lens Refractive Surgery?" Journal of Refractive Surgery; vol. 14; May/Jun. 1998; pp. 272-279.

Rosen et al.; "Staar Collamer Posterior Chamber Phakic Intraocular Lens to Correct Myopia and Hyperopia;" J. Cataract Refract. Surg.; vol. 24; May 1998; pp. 596-606.

Sanders et al; "Implantable Contact Lens for Moderate to High Myopia: Phase 1 FDA Clinical Study with 6 Month Follow-Up;" J. Cataract Refract Surg.; vol. 24; May 1998; pp. 607-611.

PCT Patentability Report for PCT/US2015/41987, dated Oct. 19, 2015.

Search Report for European Patent Application No. 15824633.0, dated Mar. 7, 2018.

* cited by examiner

Wet View

HAPTIC DEVICES FOR INTRAOCULAR LENS

REFERENCE TO RELATED APPLICATIONS

This application is a continuation-in-part of U.S. Non-Provisional application Ser. No. 12/626,473 of the same title and filed Nov. 25, 2009, which claims priority to U.S. Provisional Application No. 61/118,085 of the same title and filed Nov. 26, 2008, U.S. Provisional Application No. 61/157,781 of the same title and filed Mar. 5, 2009, and U.S. Provisional Application No. 61/184,655 of the same title and filed Jun. 5, 2009. This application also claims priority to U.S. Application No. 62/028,375 of the same title, filed Jul. 24, 2014. Each application is specifically and entirely incorporated by reference.

BACKGROUND

1. Field of the Invention

This invention is directed to haptic devices for intraocular lenses that provide increased comfort and performance to a patient. In particular, the invention is directed to haptic devices and designs, that consider a two-ring configuration within which the lens optic is held, that enhance post-surgical ocular health by maintaining separation of the anterior and posterior capsule of the human eye and therefore permit circulation of the aqueous humor within the capsule. Specifically, the invention, along with its various iterations, is designed to provide refractive stability by mitigating the extent of capsular fibrosis, and, in certain instances, mitigate the onset of other post-surgical conditions, specifically Posterior Capsular Opacification, as well as posterior segment conditions such as Age Related Macular Degeneration and Retinal Detachment.

2. Description of the Background

An intraocular lens (IOL) is an implanted lens in the eye, usually replacing the existing crystalline lens because it has been clouded over by a cataract, or as a form of refractive surgery to change the eye's optical power. The whole device usually comprises a small plastic lens with plastic side struts, called haptics, to hold the lens in place within the capsular bag inside the eye. Haptics also form the means of attachment of lenses to other areas of the eye, including the anterior angle or sulcus, the iris, and the posterior chamber ciliary sulcus. IOLs were traditionally made of an inflexible material (e.g. PMMA) though this largely been superseded by the use of flexible materials. Most IOLs fitted today are fixed monofocal lenses matched to distance vision. However, other types are available, such as multifocal IOLs which provide the patient with multiple-focused vision at far and reading distance, toric IOLs to correct for astigmatisms, and adaptive IOLs which provide the patient with limited visual accommodation.

Intraocular lenses have been used since 1999 for correcting larger errors in myopic (near-sighted), hyperopic (far-sighted), and astigmatic eyes. This type of IOL is also called PIOL (phakic intraocular lens), and the crystalline lens is not removed. More commonly, aphakic IOLs (that is, not PIOLs) are now used for visual correction errors (especially substantial hyperopia), and implanted via Clear Lens Extraction and Replacement (CLEAR) surgery. During CLEAR, the crystalline lens is extracted and an IOL replaces it in a process that is very similar to cataract surgery: both involve lens replacement, local anesthesia, both last approximately 30 minutes, and both require making a small incision in the eye for lens insertion. Patients recover from CLEAR surgery 1-7 days after the operation. During this time, patients should avoid strenuous exercise or any activity that significantly raises blood pressure. Patients should also visit their ophthalmologists regularly for several months so as to monitor the IOL implants. CLEAR has a 90% success rate (risks include wound leakage, infection, inflammation, and astigmatism). CLEAR can only be performed on patients ages 40 and older. This is to ensure that eye growth, which disrupts IOL lenses, will not occur post-surgery.

Once implanted, IOL lenses have three major benefits. First, they are an alternative to LASIK, a form of eye surgery that may not work for people with serious vision problems. Second, effective IOL implants may eliminate the need for glasses or contact lenses post-surgery. Third, the though the cataract may return, in the form of anterior or posterior capsule opactification (which results from the proliferation of lens corticular material between the capsule and the replacement lens, this may be controlled by additional surgical procedures such as an Nd-YAG laser capsulotomy. The disadvantage is that the eye's ability to change focus (accommodate) may have been reduced or eliminated, depending on the kind of lens implanted.

While significant advances have been made in the optical quality of aphakic lenses, most lenses currently made have an overall optical thickness of one millimeter or greater at the center optical focal point (e.g. see U.S. Pat. No. 4,363,142). In the late 1990's, two patents were applied for and subsequently issued for lens optics significantly thinner than the afore-referenced lens patents (U.S. Pat. Nos. 6,096,077 and 6,224,628). Although improved, the extreme thinness of the lens manufactured in accordance with U.S. Pat. No. 6,096,077 caused some minor distortions of the optic once in the eye, while the lens manufactured in accordance with U.S. Pat. No. 6,224,628 was poured of molded silicone and did not provide the desired visual acuity.

Generally, the natural lens separates the aqueous humor from the vitreous body. The iris separates the region between the cornea or anterior of the eye and the lens into an anterior chamber and a posterior chamber. The lens itself is contained in a membrane known as the capsule or capsular sac. When the lens is removed from the eye, the capsule may also be removed (capsular extraction), or the anterior portion of the capsule may be removed with the lens leaving the posterior portion of the capsule intact (extracapsular extraction). In an intraocular implant, the artificial or prosthetic lens may be inserted in the anterior chamber, the posterior chamber, or the capsular sac. The artificial lenses are usually fixedly attached within the eye, either by stitching to the iris, or by some supporting means or arms attached to the lens; in all cases the fixation mechanisms are categorized as haptics.

Several intraocular lenses designed for implant in the anterior chamber feature haptics with feet which support the lens in order to avoid the need for clips or sutures to secure the lens to the iris. The lenses work; however, sizing the lens to fit the eye is critical to avoid complications. These lenses have been made in lengths from 11.5 mm to 14 mm in 0.5 mm increments, and the thickness of the feet was about 250 microns.

A variety of lenses has been developed that provides up to four point support for the lens. The support structures for these haptics are often linked to the lens body so that the support structure should not deflect freely of the lens body, and therefore be liable to irritate portions of the eye in contact with the support structure. A variety of shapes and geometries for the lens supporting elements, or haptics, has been disclosed and described (U.S. Pat. No. 4,254,510; U.S.

Pat. No. 4,363,143; U.S. Pat. No. 4,480,340; U.S. Pat. No. 4,504,981; U.S. Pat. No. 4,536,895; U.S. Pat. No. 4,575,374; U.S. Pat. No. 4,581,033; U.S. Pat. No. 4,629,460; U.S. Pat. No. 4,676,792; U.S. Pat. No. 4,701,181; U.S. Pat. No. 4,778,464; U.S. Pat. No. 4,787,902; U.S. Pat. No. Re. 33,039; U.S. Pat. No. 4,872,876; U.S. Pat. No. 5,047,052; U.K. Patent No. 2,165,456).

Despite the advances, there remain problems with intraocular implants. For example, when an intraocular lens is inserted in the eye, an incision is made in the cornea or sclera. The incision may cause the cornea to vary in thickness, leading to an uneven surface which can cause astigmatism. The insertion of a rigid lens through the incision, even with compressible haptics, requires an incision large enough to accommodate the rigid lens (typically at least 6 mm), and carries with it the increased risk of complications, such as infection, laceration of the ocular tissues, and retinal detachment. Deformable intraocular lenses made from polymethylmethacrylate (e.g. "PMMA"), polysulfone, silicone or hydrogel may be inserted through a smaller incision. Current science and advances in surgical techniques enables incisions of less than 2 mm (micro-incision) which may prove eventually to be beneficial to the patient, though any incision of less than 3.5 mm does not require sutures.

It is preferred that the intraocular lens be capable of insertion through a small incision. U.S. Pat. No. 4,451,938 shows an intraocular lens in which the lens body is made in two pieces so that each piece may be inserted through the incision separately and then joined by dowels after insertion in the eye. U.S. Pat. No. 4,769,035 discloses a foldable lens which may be inserted through an incision about 3.5 mm in length.

When the intraocular lens is inserted in the anterior chamber of the eye, the feet of the haptics, or lens supporting elements, generally lodge in the scleral sulcus, a depression anterior to the scleral spur where the iris and the ciliary muscle join the sclera in the angle of the anterior chamber. The scleral sulcus is crossed by trabecular tissue in which are located the spaces of Fontana. The anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The lens should be positioned so the flow of fluid through the trabecular tissue is not blocked or glaucoma may result.

Since the feet of the haptics of anterior chamber lenses rest in the scleral sulcus, the flow of fluid is blocked where the feet are in contact with the trabecular tissue. It is therefore desirable to decrease the amount of surface area of the haptic foot in contact with the trabecular tissue. At the same time, the haptic feet have sufficient height to prevent adhesive tissue or synechia from growing around the feet and anchoring them to the iris or cornea. The opening of the trabecula is about 200 microns, and the haptic feet of conventional intraocular lenses are usually on the order of 175 to 200 microns, effectively blocking the openings in the trabecula wherever the feet are in contact with the tissue.

Other lenses that are situated in the posterior chamber may attach to the ciliary sulcus or be positioned in the equator of the capsular sac. In haptics with attachment to the ciliary sulcus, appropriate dimensioning is essential to ensure proper anchoring. In haptics with attachment to the capsular equator, recent science demonstrates the need for appropriate dimensioning also, as the haptic must place the lens properly in the capsule. If the haptic is too short for the capsule, the lens can dislodge or rotate in the eye, events that can require additional surgery to correct and can also cause intraocular trauma. Additionally, haptics that are too short for the capsule do not allow the lens to provide the patient with any desired or designed focal flexibility (that is, accommodation). If the haptic is too long for the capsule, the lens can angle either posteriorly or anteriorly at a greater angle than designed, in the former case significantly reducing visual acuity at distance and risking reverse accommodation, in the latter case putting pressure on the iris and diminishing focal flexibility.

U.S. Pat. Nos. 5,258,025 and 5,480,428 describe a lens surrounded by a sheet-like "positioner" having projections called "supporting elements either at the four corners of or continuously around the positioner, the supporting elements being 0.3 mm long and 0.01 to 0.05 mm thick (7"a and 7"b of FIG. 3 of the '025 patent, 18 of the '428 patent). However, the lens is for implantation in the posterior chamber, the lens of the '428 actually having a length short enough to "float." In addition, the sheet-like nature of the positioner prevents independent deflection of the feet in response to forces applied by the eye.

In addition, the lens may place a greater or lesser degree of force on the haptic feet as the lens is compressed, depending upon construction of the lens. Since the amount of pressure for a given surface area is proportional to the force, it is desirable to decrease or distribute the amount of force placed on the haptic feet in order to diminish the force applied by the feet on the trabecular tissue. This goal is achieved by mounting the haptic arms on the ends of a flexible support bar in cantilever fashion, the support bar being offset from the lens body by a stem.

The act of surgically removing the natural lens and replacing it with an intraocular lens of whatever design gives rise to certain other possible conditions that can have a profound impact on the patient's ability to see clearly over a protracted period of time, the extent of focal accommodation that can be provided to the patient, and the effective positioning of the replacement lens in the eye. These conditions normally occur in a majority of cases but may be able to be mitigated with inventive lens and haptic designs. In particular, ophthalmologists have observed that the lens capsule will tend to atrophy over time. This is in part attributable to the fact that the replacement lens rarely occupies the entire lens capsule, and most lenses tend to flatten out the capsule, thus allowing the anterior and posterior surfaces of the capsule to adhere together, causing capsular fibrosis, atrophy, hardening, and adhesions. All these will necessarily diminish the effectiveness of any lens claiming to offer focal accommodation. In addition, it is possible that such fibrosis will cause the intraocular lens to re-position, either anteriorly or posteriorly, tilt, or decenter, any of which could cause significant change in the patient's refractive correction and quality of vision. It is possible that increased circulation of the aqueous humor can preserve the suppleness of the natural lens capsule, and preventing contact between the capsular surfaces should prevent capsular fibrosis, thereby protecting the integrity of the patient's refractive correction and overall visual acuity.

Some physicians have advocated the use of capsular tension rings to prevent capsular atrophy. However, these rings, which are situated in the lens equator, do not allow the ciliary body to influence the dimensions of the lens so as to provide for focal accommodation. Thus, whereas capsular retention rings may be effective when used in conjunction with non-accommodating or multifocal lenses, their value with premium lenses that claim accommodation is questionable.

In some cases post surgical adhesions can occur between the lens capsule and the haptic of the intraocular replacement lens. If significant enough, these adhesions can diminish the focal accommodative functions of the lens.

Posterior Capsule Opacification (PCO) is a condition that occurs in approximately 50% of cataract patients within three years after surgery. PCO is caused by the natural migration of lens epithelial cells from the anterior lens capsule to the equator Once the epithelial cells reach the equator, the cells die off leaving proteins of lens corticular material that accumulate on the posterior capsular surface in the form of Elschnig's pearls or of Soemmering's Rings. These fibroblasts that adhere to the capsule can cause significant shrinkage, and clouding of the lens. If the PCO migrates to the optical area of the capsule, vision is significantly impaired. The occurrence of PCO can be mitigated surgically by means of Nd-YAG-Laser correction, which perforates the posterior capsule with a hole that opens the optical zone of the posterior capsule. However, Nd-YAG laser capsulotomy surgery also carries risks of post-surgical complications including possible prolapse of the vitreous into the capsule (which can precipitate retinal detachment), and, as such, should be avoided if possible.

In the case of the inventive haptic designs incorporated herein, the inventors believe that the onset of PCO may be delayed or eliminated altogether through the use of appropriate haptic design to deter epithelial cell migration. In particular, 1) a haptic design that keeps the capsule open and prevents contact between the anterior and posterior surfaces may assist in mitigating PCO onset by maintaining hydration of the capsule, 2) the quality of the cataract or CLEAR surgery can assist in retarding PCO through assiduous cleaning and polishing of the anterior capsule, 3) the positioning of certain retention rings against the anterior of the capsule may arrest the migration of epithelial cells which cannot release their proteins until and unless they reach the fornix (equator) of the capsule; research demonstrates that if lens epithelial cells are dislodged from the anterior capsule they do not reattach, and 5) the positioning of certain retention rings in the fornix or against the posterior capsule may act to retain any corticular protein blasts at the periphery of the posterior capsule, and thereby prevent their aggregation in the posterior capsular optic zone. In some cases, IOL designers have found some success at mitigating the onset of PCO by configuring the posterior surface of the lens so as to provide a right angle at the junction of the lens with the posterior capsule. This configuration may be particularly applicable for those lenses that rest entirely against the posterior capsule and do not accommodate. In other cases, IOL designers have determined that the surface quality of the haptic may have some influence on PCO mitigation, though this topic continues to be debated. It is generally observed that absence of capsular fibrosis may also contribute to post-surgical capsular health and patient well-being.

SUMMARY OF THE INVENTION

The present invention overcomes the problems and disadvantages associated with current strategies and designs and provides new haptic devices and methods for positioning an intraocular lens in the eye, as well as designs for specific functionality to provide optimal focal flexibility and mitigate common post surgical problems.

An embodiment of the invention is directed to haptic devices that are comprised of two parallel rings connected by a pillar or several pillars of haptic material, between which an optic is suspended, such that the anterior ring makes contact with the anterior capsule at some distance from the lens equator, and the posterior ring makes contact with the posterior capsule at some distance from the lens equator, the rings connected to each other and to the framework supporting the lens optic by means of ribbons and struts that maintain suitable spacing between the rings and provide for proper positioning of the lens within the capsule. The functionality of the anterior ring is to arrest epithelial cell migration across the anterior capsule, thus preventing these cells from maturing and arriving at the capsular equator. Another functionality of the inventive anterior ring is to respond to the changes of the ciliary body in such a manner as to enable the forward motion of the lens optic within the capsule to accommodate for near vision. The functionality of the posterior ring is to protect the posterior optic zone from PCO by maintaining a suitable barrier between any pearls or fibroblasts that may develop over time and block their incursion into the area behind the lens optic. Another functionality of the posterior ring is to capture the physical forces of the ciliary body and work in conjunction with the anterior ring, the struts and the ribbons of the haptic to allow the lens optic to move within the capsule to adjust to the various stages of focal accommodation. Another functionality of the posterior ring, together with the anterior ring, the struts and ribbons is to maximize the natural circulation of the aqueous humor so as to preserve hydration throughout the lens capsule and the aqueous humor. This hydration may have the additional desirable effect of providing a mechanism whereby the spent and arrested epithelial cells can be flushed away by the aqueous humor and disposed of through the trabecular meshwork.

Another embodiment of the inventive haptic is a solid circle haptic into which are cut arced channels, preferably five, that extend from the anterior ring to the edge of the optic. These channels allow the optic to move in accommodation without distortion or decentralization, while the anterior and posterior haptic rings fix the lens centered in the capsule and maintain the capsule open.

Another embodiment of the inventive haptic is to provide for a series of easements in the struts connecting the anterior and posterior haptic rings whereby the level of force exercised on the lens is commensurate with the desired degree of accommodative movement of the lens within the eye.

Another embodiment of the invention is directed to a method of securing a lens in a mammalian eye comprising removing a natural lens from a mammalian eye; and inserting a lens comprising the haptic of the invention into the mammalian eye.

Another embodiment of the invention is directed to devices, such as insertion devices, and methods of inserting a haptic into a lens envelope of a mammalian eye comprising the haptic of the invention.

Other embodiments and advantages of the invention are set forth in part in the description, which follows, and in part, may be obvious from this description, or may be learned from the practice of the invention.

DESCRIPTION OF THE INVENTION

Figure 1A:
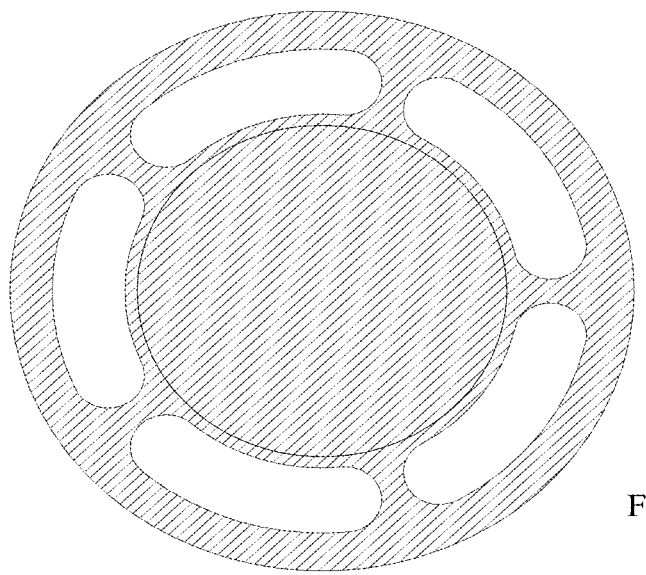
FIGS. 1A-B illustrate an open loop haptic design (kidney haptic) with full anterior and posterior rings.

The haptic device is used to affix an intraocular lens within the lens capsule once the natural crystalline lens has been removed surgically. The three specific design purposes of the haptic are: i) to permit the lens to be implanted in the eye by means of an injector through an incision of less than about 3 mm; ii) to allow the lens to move within the posterior chamber of the eye in order to provide focal flexibility to the patient; and iii) to affix the lens in the lens capsule in such a way as to minimize the risk of Posterior Capsule Opacification ("PCO"), a negative consequence of lens replacement procedures that currently occurs in approximately 50% of patients within 2 to 3 years after surgery, iv) to maximize circulation of the aqueous humor within the lens capsule to minimize capsular fibrosis, and v) to provide a safe and comfortable framework for lenses with different styles of optics, with the objective of preserving as much as possible the natural physiognomy of the eye. Although intraocular lenses have been successfully implanted for several decades now, many of the haptic designs do not produce the desired results of mitigating PCO, reducing capsular fibrosis, presering the integrity of the vitreous humor and posterior segment, and/or facilitating focal flexibility (or the ability of the patient to adjust far to near vision and minimize the need for reading glasses).

A haptic device design has been surprisingly discovered that that ameliorates PCO and significantly deters capsular fibrosis. In one embodiment, the haptic of the invention consists of a pair of rings connected to each other by pillars of haptic material, and to the optic by struts or bands of the same material as the attached lens, which preferably may be any of polymethylmethacrylate, hydrophobic or hydrophilic acrylate, silicone, or blends of these materials (or of the same material as the lens).

In this embodiment, a haptic design has been surprisingly discovered that has anterior and posterior haptic feet that comprise entire rings that rest on the anterior and posterior capsules, respectively, maintaining the entire capsule open and creating a barrier at both the anterior and the posterior capsular surfaces to prevent migration of epithelial cells. In this embodiment, the haptic feet are connected by a series of struts that have open spaces between, preserving the designed distance between the rings and providing for optimal fluid circulation around the inventive lens. In this embodiment also, the anterior and posterior rings may be configured so as to arrest epithelial cell migration across the anterior capsule and incursion of PCO into the optical zone of the posterior capsule, thereby providing the potential for the patient to use the intraocular lens for a substantial period of time without adverse consequences. In this embodiment, easements may be made in the struts to accommodate smaller than normal capsules, thus providing for stable concentration of the lens optic notwithstanding potential capsular size differences or changes over time. In this embodiment additionally certain easements may be made in the inner surface of the anterior and posterior rings so as to provide for responsiveness of the lens haptic to the muscular prompts of the ciliary body.

In these embodiments, the entire dimension of the lens, including both haptics and the optic, preferably varies depending upon the measurement of the natural lens capsule. The haptic has varying points of individual tailoring, including the length of the ribbon haptic (2) and (3), and the dimension of the solid end portion of the haptic. Additionally, the haptic may be used for veterinary purposes, and its overall dimensions may be increased or reduced to fit in the lens capsule of various animals.

In the embodiments disclosed herein, rings may also be affixed to the anterior and or posterior joints or legs of such angled segments to rest in the capsule at some distance from the equator, or with one ring in the equator and the other at some distance, to mitigate the migration of epithelial cells. In such cases the rings may contain right angles at the areas of contact with the anterior or posterior surface of the capsule. The function of such rings in conjunction with the angled segments may also be to maintain the aperture of the lens capsule distant from the equator so as to provide for continuous irrigation of the region by the normal circulation mechanisms of the aqueous humor. This may preserve the natural consistency and elasticity of the lens capsule, thus ensuring prolonged functionality of the inventive lens haptic.

One function of the anterior retention ring is to arrest epithelial cells that are migrating along the anterior capsule. When these epithelial cells are removed from the capsular wall they lose their ability to adhere to any surface (i.e. once detached are not re-attachable). This means that with a barrier along the anterior capsule the number of epithelial cells that arrive at the equator can be limited whence they release cortical material that can cause PCO. The posterior ring limits the extent of PCO incursion, whereas the anterior ring limits PCO creation.

Preferred materials for the intraocular lens comprises hydrophilic acrylic, hydrophobic acrylic, silicone or other suitable, and preferably a flexible material that is approved for intraocular use. Preferred materials retain sufficient molecular memory to provide for constant positioning of the lens against the inner capsular wall. It is also preferred that the acrylic material be flexible enough to change shape easily and respond to the prompts of the ciliary body, but resilient enough to resist cracking or other deterioration for decades. Contact and continued contact of the haptic rings with the lens capsule strongly hinders and even prevents migration of epithelial cells along the anterior capsule to the equator, which is the cause of Posterior Capsular Opacification (or PCO) in many post-cataract surgery patients. The preferred design also maintains the open lens capsule, thus preventing the possibility of adhesions between the anterior and posterior surfaces of the capsule. Further, the open capsule also allows the aqueous humor to circulate within the capsule, which provides for enhanced hydration of the lens capsule. This enhanced hydration provides a significant advantage over models of intraocular lenses that are primarily two-dimensional in their configuration and which stretch the lens capsule out horizontally.

Figure 1B:
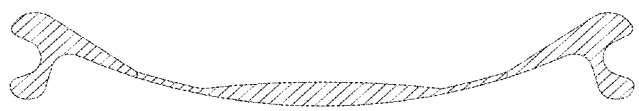
Figure 2A:
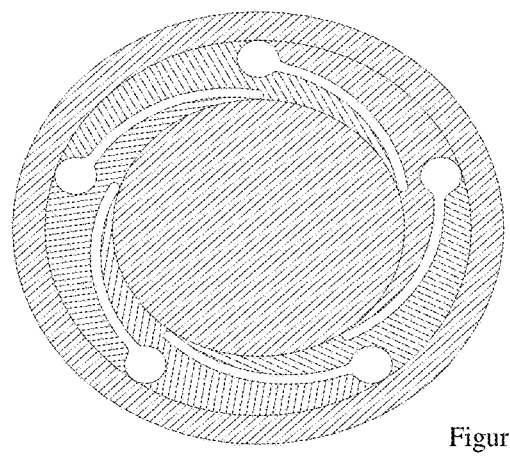
FIGS. 2A-B illustrate a full circle haptic with arced grooves.
Figure 2B:

FIGS. 1A-B depict both top and sagittal views of the full circular haptic with ribbons and struts to create oval openings between the optic and the haptic rings. The number of contained ovals and the precise configuration of such ovals may vary according to the designed intent of the inventive haptic.

FIGS. 24A-B depict both top and sagittal views of a full circular haptic with arced grooves of material removed so as to provide for focal flexibility and fluid flow. In this case the number of grooves and the length and configuration of such grooves may vary in accordance with the intended purpose of the designed haptic.

Figure 3:
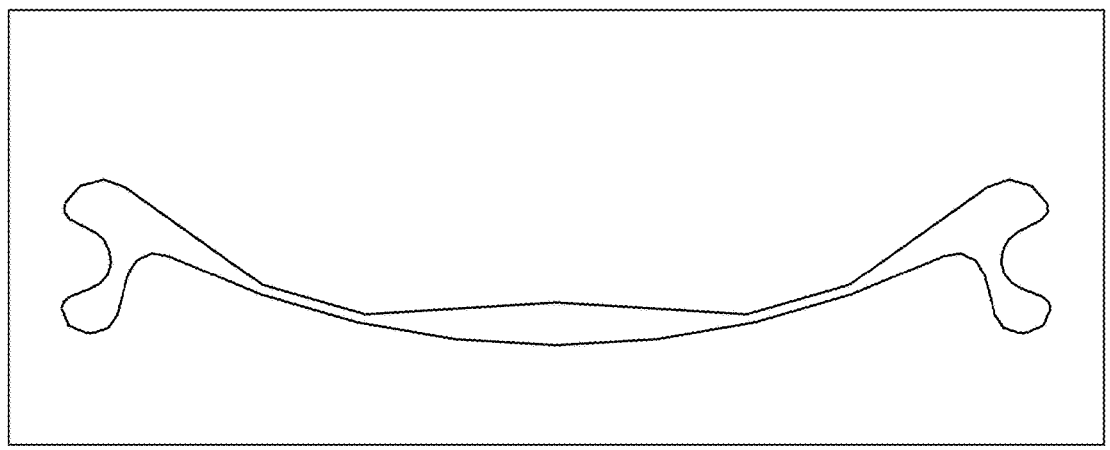
FIG. 3 illustrates another embodiment of the invention showing a lens design in cross section.
Figure 4:
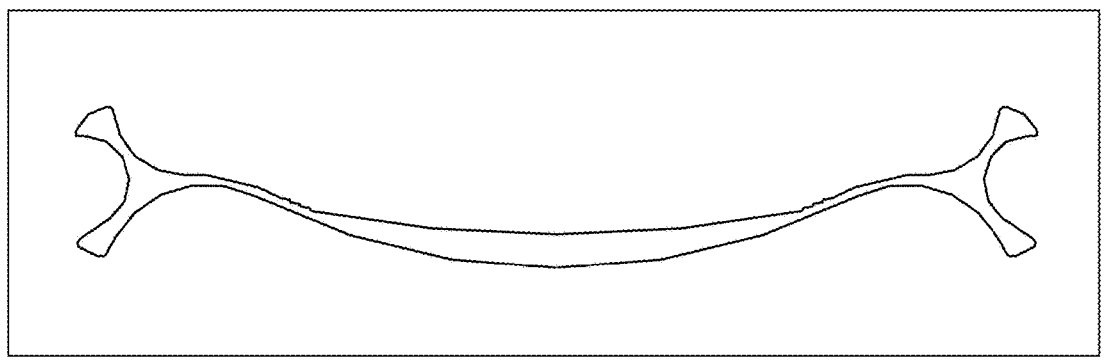
FIG. 4 illustrates another embodiment of the invention showing a lens design in cross section.
Figure 5:
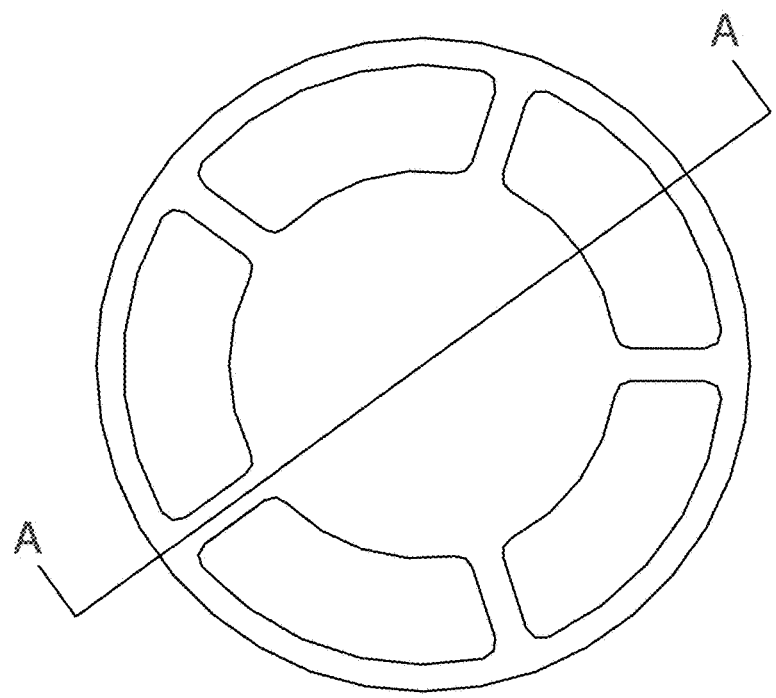
FIG. 5 illustrates another embodiment of the invention showing a top view of a lens design.
Figure 6:
FIG. 6 illustrates the cutaway of FIG. 5.

FIGS. 3 and 4 illustrate an embodiment of the lens, both shown in cross section. FIG. 5 depicts a top view of the embodiment of the lens showing full circle anterior and posterior rings. Haptic pillars connect the rings to the haptic arms and preferably only at the haptic arms. Preferably the aperture to the fornix is significant and hydration occurs through the capsule. Also preferably, the anterior and/or posterior rings have modestly sharper edges at the contact points with the capsule. Preferably the lens is positioned close to the nucleus of the position of the natural lens and the center optic rests against the posterior capsule. The optic of this embodiment is preferably about 6 mm in diameter. Overall, this optic may provide significant improvement to depth of field vision. FIG. 6 illustrates a transverse cross section from point A to A as shown in FIG. 5.

Figure 7:
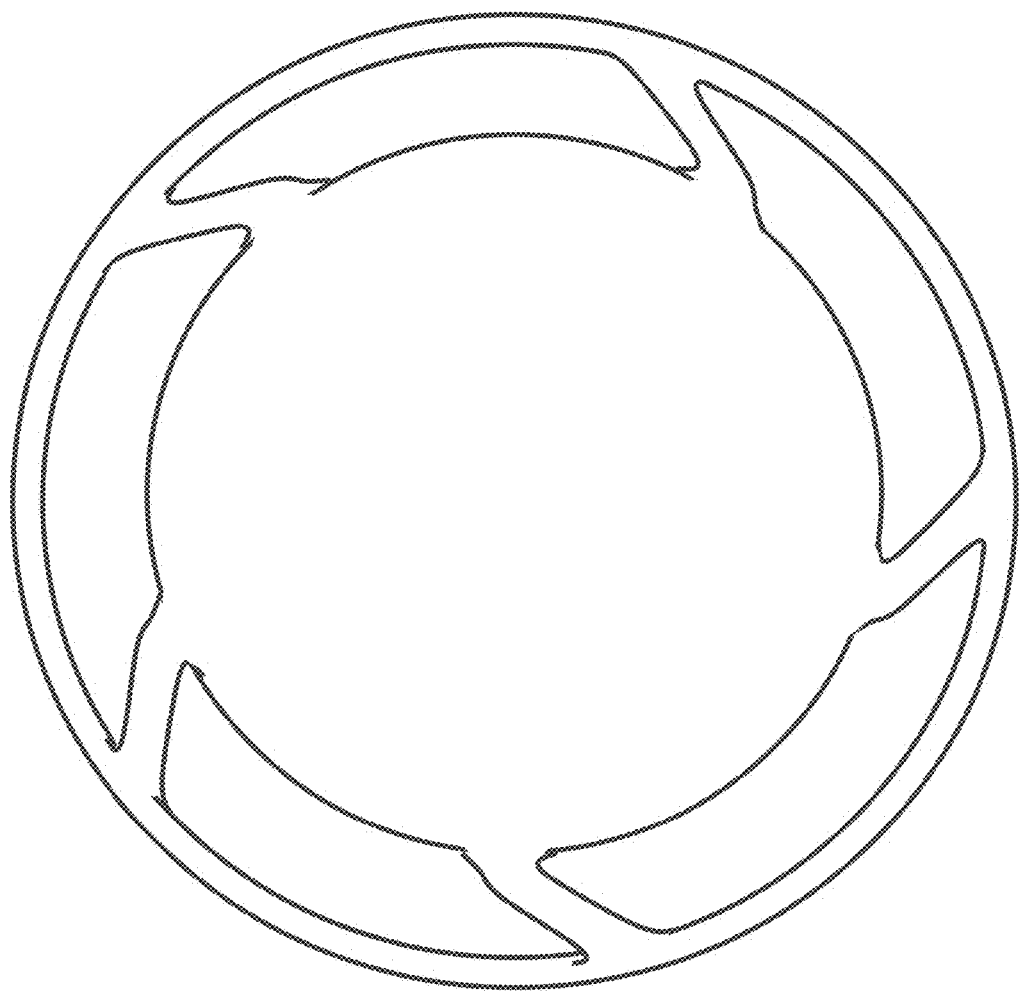
FIG. 7 illustrates a lens with spiral anterior and posterior haptics.
Figure 8:
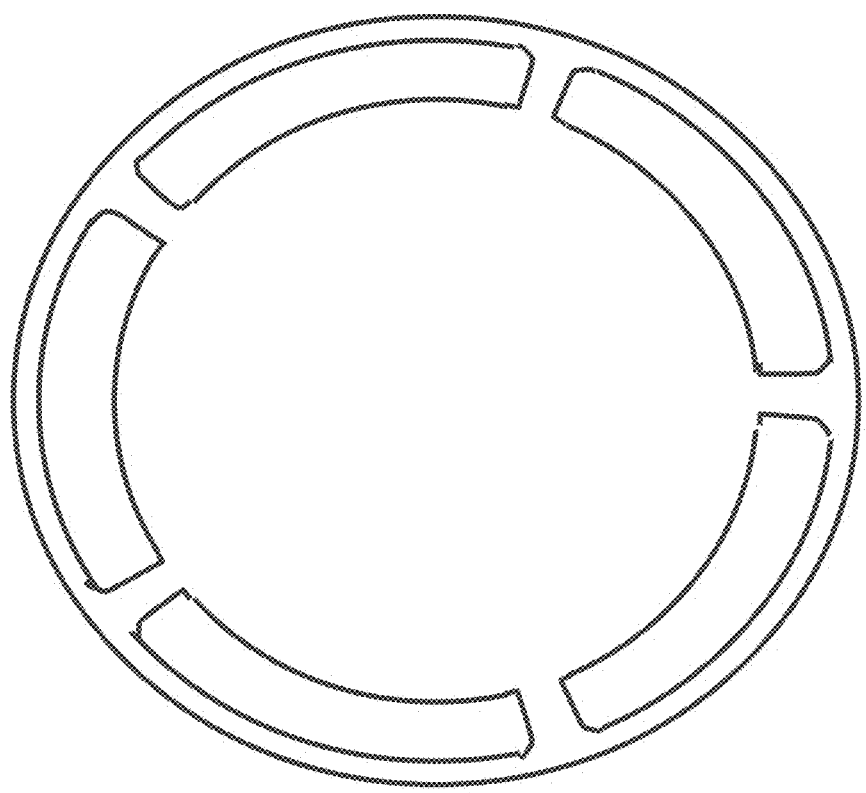
FIG. 8 illustrates a lens with straight anterior and posterior haptics.
Figure 9:
FIG. 9 illustrates a posterior pillar system designed to bend if necessary to adjust to different capsular dimensions.

FIGS. 7-9 illustrate additional embodiments of inventive lenses. The lens depicted in FIG. 7 has spiral anterior and posterior haptics. The haptic bridges supporting the anterior and posterior rings are angled so as to provide for some posterior compression in the event of a smaller than average capsular circumference. FIGS. 8 and 9 depict a lens without the angled haptic bridge supports. FIG. 9 is a cross-section of the lens of FIG. 8. Preferably the lens has a thick anterior haptic to buttress the anterior ring, a flat anterior surface to minimize step height, and a thin bendable posterior haptic. While two shapes of haptic bridge supports are shown other haptic bridge support shapes can be used.

Figure 10:
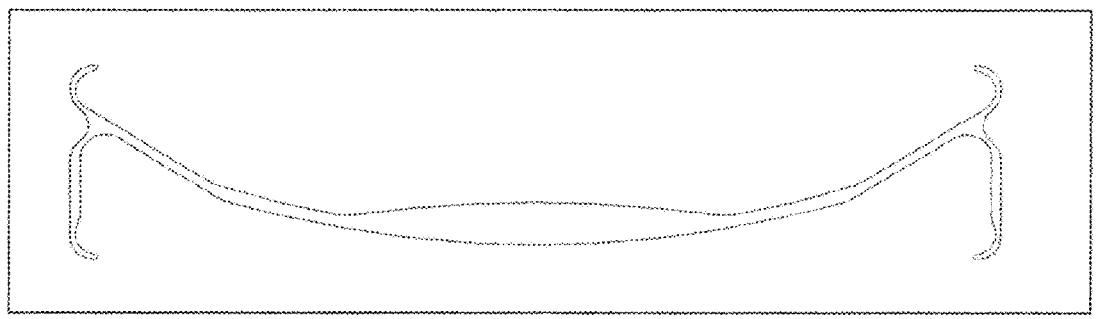
FIG. 10 illustrates an embodiment of the invention showing a lens in cross section wherein the uppermost haptic is comprised of the anterior ring designed to come into contact with the anterior capsule surface, thereby arresting lens epithelial cells' migration along the anterior capsule to the fornix.

FIG. 10 illustrate an inventive lens shown in cross section whose uppermost haptic is comprised of the anterior ring designed to come into contact with the anterior capsule surface, thereby arresting lens epithelial cells' migration along the anterior capsule to the fornix. This anterior ring is designed with an inventive curvature such that the ring continually maintains contact with the anterior capsule in both a distance and near vision state and in all intermediate states. The lowermost portion of the inventive haptic is comprised of the posterior ring designed to maintain contact with the posterior capsule at a point distally outward of the optical zone, thereby preventing incursion of posterior capsule opacification into the optical zone of the posterior capsule. The haptic pillar connecting the anterior and posterior rings may be solid or may have apertures cut into it, in the case of the former design, to restrict any posterior capsule opacification to the area of the fornix, or capsular equator, and in the case of the latter to permit hydration of the entire lens capsule by allowing circulation of the aqueous humor throughout the capsule. The inventive lens haptic suspends the optic posteriorly from a haptic that is connected to the haptic pillar and is placed posterior to the anterior haptic ring so as to prevent the lens optic from coming into contact with the anterior capsule. The haptic supporting the optic may be perforated in different patterns and at different intervals so as to allow circulation of the aqueous humor as well as permit the optic to move anteriorly and posteriorly within the capsule in response to the natural movements of the ciliary body so as to provide focal accommodation.

Figure 11A:
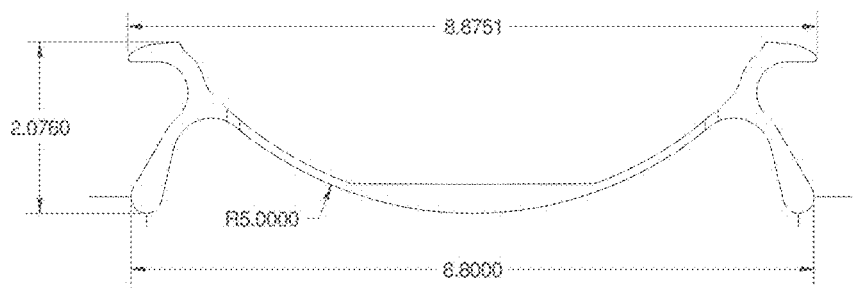
FIGS. 11A-B illustrate an embodiment of the invention having one orientation tab and containing the presence of a small fin on the inner anterior surface of the anterior ring designed to create a sharper edge for arrest of migrating lens epithelial cells.
Figure 11B:
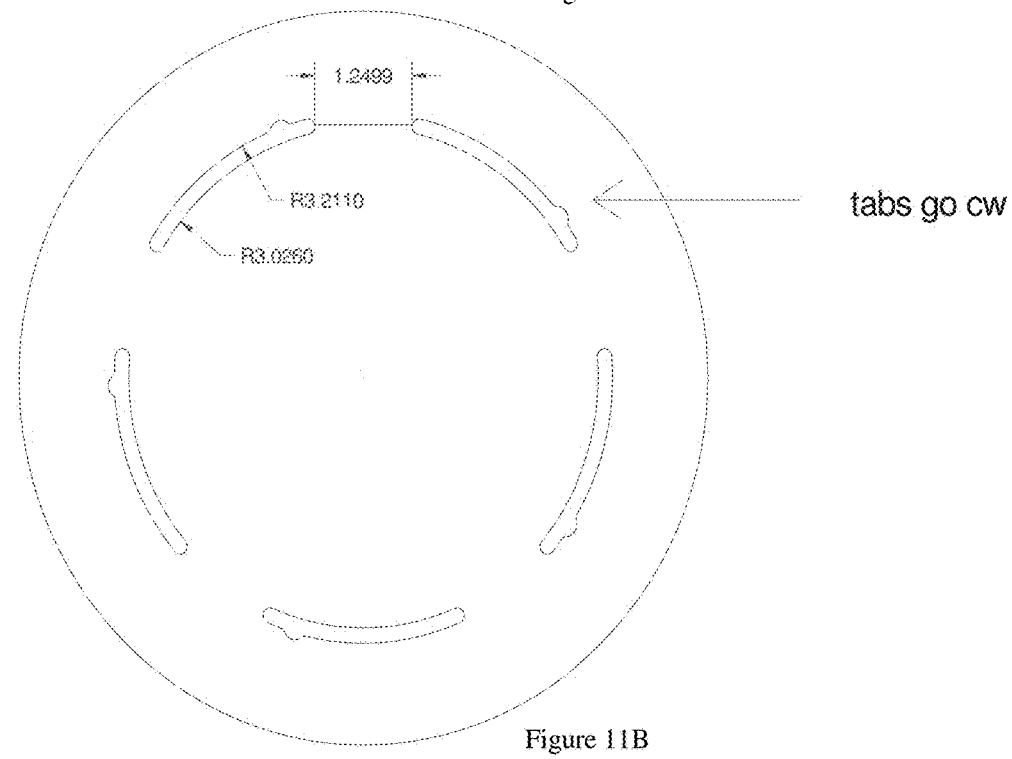
Figure 12A:
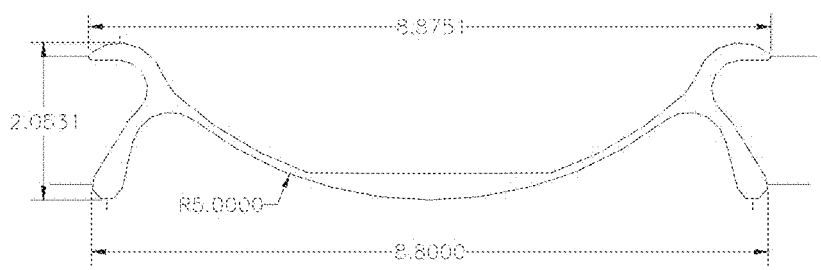
FIGS. 12A-B illustrate another embodiment of the invention having an orientation tab.
Figure 12B:
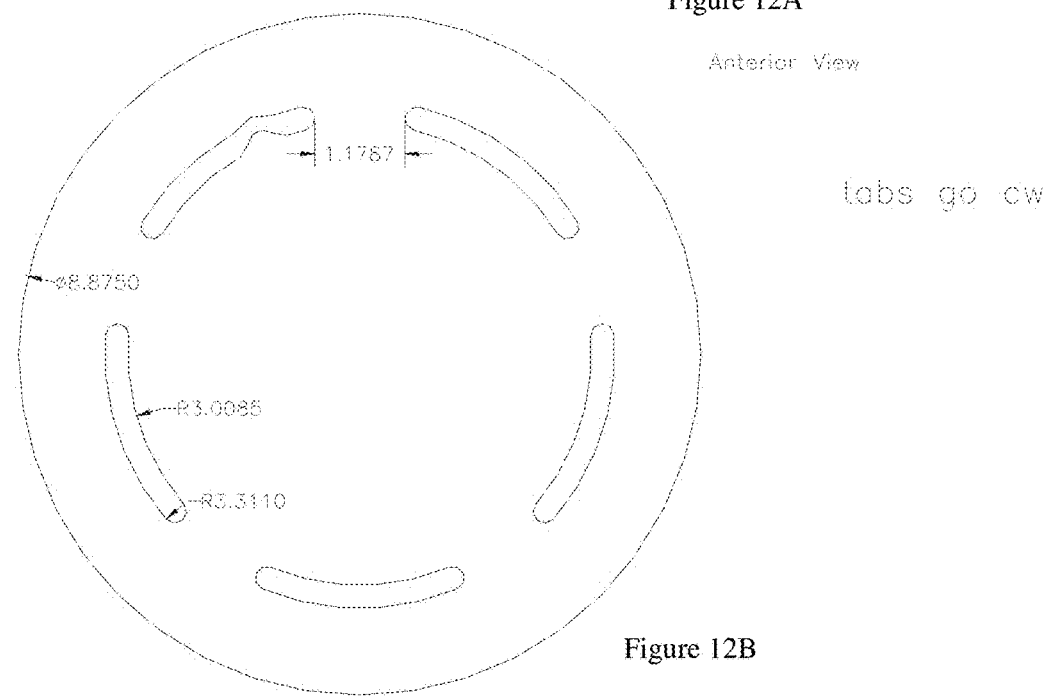

FIGS. 11A-B and 12A-B depict embodiments of an IOL having orientation tabs. While any IOL disclosed herein can have orientation tabs, FIGS. 11A-B and 12A-B are examples of the IOL in FIG. 1 with orientation tabs. Preferably, as shown in FIG. 11B, the IOL has a plurality of orientation tabs. For example, as shown in FIG. 11B, each opening between the lens and the haptic ring may have an orientation tab positioned therein. However, as shown in FIG. 12B, there may be only one orientation tab. Preferably, when positioned in the eye, the orientation tabs will indicate a proper anterior and posterior position. For example, as shown in the figures, when properly implanted, the orientation tabs will be toward the clockwise end of the opening. The orientation tabs may project into the opening or extend from the opening into the IOL, or combinations thereof.

Figure 13A:
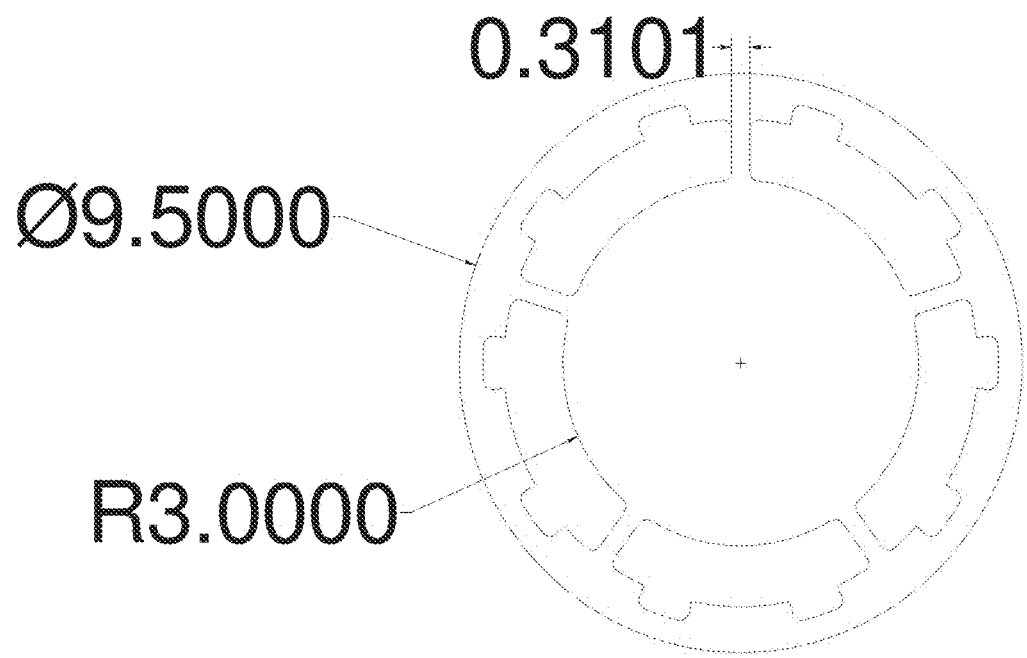
FIGS. 13A-B illustrate another embodiment of the invention.
Figure 13B:
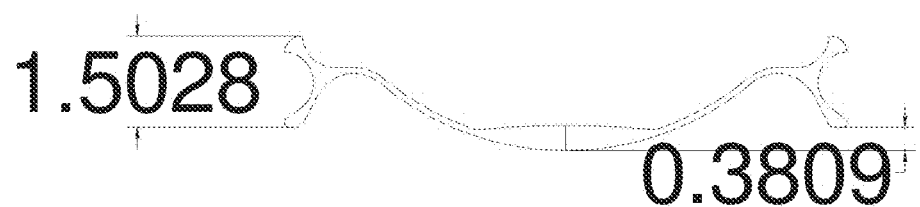

FIGS. 13A-B depict embodiments of an IOL having fenestrations. While any IOL disclosed herein can have fenestrations, FIGS. 13A-B are examples of the IOL in FIG. 1 with orientation tabs. Preferably, as shown in FIG. 11A, the IOL has a plurality of fenestrations. For example, as shown in FIG. 11A, each opening between the lens and the haptic ring may have a pair of fenestrations positioned to extend into the haptic ring. Each opening may have more or fewer fenestrations. Preferably, the fenestrations reduce the amount of material used in the IOL and thereby reduce the weight of the IOL. Preferably, the fenestrations extend out to the fornix of the IOL.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. An intraocular lens, comprising:
   an optic;
   a plurality of haptic arms extending from the optic;
   an annular ring coupled to the plurality of arms, wherein the annular ring is comprised of an anterior retention ring and a posterior retention ring, wherein the plurality of haptic arms define openings between the annular ring and the optic; and
   one pair of orientation tabs positioned off center within one of the openings, a first orientation tab of the pair of orientation tabs extending radially away from the optic and into the annular ring, and a second orientation tab of the pair of orientation tabs extending away from the optic along the same radius as the first orientation tab and into a surface of the one opening, the pair of orientation tabs indicating an alignment of the intraocular lens when placed in an eye.

2. The intraocular lens of claim 1, wherein the anterior retention ring and the posterior retention ring are separated by a plurality of haptic pillars.

3. The intraocular lens of claim 2, wherein each haptic pillar is coupled to one of the plurality of haptic arms.

4. The intraocular lens of claim 2, further comprising gaps between the haptic pillars.

5. The intraocular lens of claim 1, which is comprised of a hydrophilic acrylic, hydrophobic acrylic, silicone, or combinations thereof.

6. The intraocular lens of claim 1, which is comprised of a material for insertion into the eye.

7. The intraocular lens of claim 1, further comprising a haptic ribbon coupling the optic to the haptic arms.

8. The intraocular lens of claim 7, wherein the haptic ribbon has one or more rounded corners.

9. The intraocular lens of claim 1, wherein each haptic arm extends from a circumference of the optic to an inner surface of the annular ring.

10. The intraocular lens of claim 1, wherein the optic and the annular ring are coaxial.

11. The intraocular lens of claim 1, wherein the openings have a smaller radial width than circumferential length.

12. The intraocular lens of claim 1, wherein the anterior retention ring and the posterior retention ring are connected at an apex of a "U" shaped recess in an outer circumferential surface of the annular ring.

13. The intraocular lens of claim 12, wherein the posterior haptic ring is coupled posteriorly to the anterior retention ring.

14. The intraocular lens of claim 1, wherein the annular ring has a kidney shaped cross section.

15. The intraocular lens of claim 1, which is adapted to be compressed by an instrument to allow insertion into the eye.

16. The intraocular lens of claim 1, wherein the annular ring, when inserted into the eye, is adapted to move in response to movement of a ciliary process.

17. The intraocular lens of claim 16, wherein movement of the annular ring provides focal accommodation.

18. The intraocular lens of claim 1, wherein the pair of orientation tabs is positioned between two of the plurality of haptic arms.

* * * * *